United States Patent [19]
Kato et al.

[11] Patent Number: 4,917,480
[45] Date of Patent: Apr. 17, 1990

[54] EYE REFRACTIVE POWER MEASURING APPARATUS

[75] Inventors: Yasuo Kato; Kiwami Horiguchi; Ikuo Kitao; Yoshihiro Takahashi, all of Tokyo, Japan

[73] Assignee: Kabushiki Kaisha TOPCON, Tokyo, Japan

[21] Appl. No.: 277,439

[22] Filed: Nov. 28, 1988

Related U.S. Application Data

[63] Continuation of Ser. No. 153,506, Feb. 3, 1988, abandoned, which is a continuation of Ser. No. 819,607, Jan. 17, 1986, abandoned.

[30] Foreign Application Priority Data

Jan. 18, 1985 [JP] Japan ................................. 60-5782
Jun. 22, 1985 [JP] Japan ............................... 60-136517

[51] Int. Cl.⁴ ......................... A61B 3/02; A61B 3/10
[52] U.S. Cl. ..................................... 351/211; 351/237
[58] Field of Search ............... 351/205, 211, 222, 237, 351/238, 241, 243

[56] References Cited

U.S. PATENT DOCUMENTS

3,525,565  8/1970  O'Neill et al. ....................... 351/211
4,173,398  11/1979  Okamoto et al. .................... 351/211
4,277,150  7/1981  Wada et al. .
4,293,199  10/1981  Wada et al. .......................... 351/211
4,304,468  12/1981  Wada .
4,306,778  12/1981  Wada et al. .

Primary Examiner—Rodney B. Bovernick
Assistant Examiner—J. Ryan
Attorney, Agent, or Firm—Finnegan, Henderson, Farabow, Garrett & Dunner

[57] ABSTRACT

An eye refractive power measuring apparatus is disclosed. It includes a chart projection system for projecting a chart image for test use to a retina of an eye under test by using visible light, a measuring target projection system for projecting a measuring target image to the retina of the eye under test by using invisible light, a display device for displaying the measuring target image as a visible image, a focussing state of the measuring target image being made changeable simultaneous with change of a focussing state of the chart image for test.

5 Claims, 7 Drawing Sheets

EYE REFRACTIVE POWER MEASURING APPARATUS

This application is a continuation of application Ser. No. 153,506, filed Feb. 3, 1988, now abandoned, which is a continuation of application Ser. No. 819,607, filed Jan. 17, 1986, now abandoned.

BACKGROUND OF THE INVENTION

This invention relates to an eye refractive power measuring apparatus for measuring the eye refractive power of an eye under test by projecting a chart image for test use to the retina of the eye under test by using a visible light and judging the response of a patient.

Heretofore, there has been known the so-called subjective type in an eye refractive power measuring apparatus for measuring an eye under test, wherein a chart for test use is shown to a patient, a correction lens is moved to a position where the patient is supposed to see the chart correctly by judging the response of the patient, and the refractive power of the eye under test is measured from the refractive power of the correction lens. That is, a tester or oculist is required to effect the measurement based solely on the response of the patient and without his own recognition of the chart image on the retina of the eye.

By the way, in the eye refractive power measurement, it is not only required to measure refractive power but there is a case where it is required to measure how close to a near point position the eye under test can still enact its accommodation.

In such a case as mentioned above, according to the aforementioned conventional apparatus, the refractive power of the eye under test is corrected based on what is obtained by measurement, a chart for eyesight test use is moved to the near point position in the foregoing state, and amplitude of accommodation is measured by judging the response of a patient at that time.

There is also known another type of an eye refractive power measuring apparatus for both subjective and objective use, wherein the aforementioned subjective type refractive power measuring apparatus is incorporated in the so-called objective type refractive power measuring apparatus in which a measuring target image is projected to an eye under test by using invisible light and the refractive power of the eye under test is measured in an objective fashion by opto-electrically detecting the focusing state of the target image.

However, in any one of the above-mentioned conventional eye refractive power measuring apparatuses, the tester cannot observe the chart image for test use projected to the retina of an eye under test. Since the tester is required to carry out the test by guessing the patient's condition under which he gazes at the chart through question and answer exchanged between the tester and the patient, a long experience and a good perception are required in order to carry out an accurate measurement.

In the measurement for amplitude of accommodation, the amplitude of accommodation is measured based solely on the response of the patient, and the patient himself cannot know how far the accommodation is actually enacted, thus making it difficult to carry out an accurate measurement.

SUMMARY OF THE INVENTION

The present invention is accomplished in order to solve the above-mentioned problems involved in the prior art.

In order to solve the above problems, a first embodiment of the invention includes a chart projection system for projecting a chart image for subjective test use to a retina of an eye under test by using visible light, a measuring target projection system for projecting a measuring target image to the retina of the eye under test by using invisible light, an observation system for observing the measuring target image after converted to a visible image, a focusing state of the measuring target image being made changeable simultaneous with change of a focusing state of the chart image for test use, and an indicator display device for displaying the target image as a visible image.

A second embodiment of the invention includes a chart projection system for projecting a chart image for test use to a retina of an eye under test by using visible light, a measuring target projection system for projecting a measuring target image to the retina of the eye under test by using invisible light, an observation system for observing the measuring target image after converted to a visible image, a focusing state of the measuring target image being made changeable simultaneous with change of a focusing state of the chart image for test use, and accommodation measuring system for measuring amplitude of accommodation based on change of focusing state of the measuring target image to be observed by the observation system according to change of focusing state of the chart image for subjective test use.

Since the present invention is constituted as mentioned above, a target image of invisible light is projected to the retina of an eye under test at the same time when a chart image for subjective test use is projected, the target image formed on the retina of the eye under test is indicated on an indicator portion based on the foregoing, and a tester can recognize the refractive state of the eye under test from the target image during testing. If an index plate disposed at a far point position is projected as a measuring target image to the retina of the eye under test by using invisible light, at the same time a chart image disposed at a far point position is projected to the retina of the eye under test by using invisible light, and thereafter a chart plate or a projection lens of a chart projection system is moved to the near point position direction, although the measuring target image is split, since the position where the split image is first observable becomes the near point position, the patient can recognize the difference between the near point position and the far point position as amplitude of accommodation and at the same time the tester can obtain the amplitude of accommodation in quantity.

DETAILED DESCRIPTION OF THE EMBODIMENTS

A preferred embodiment of an eye refractive power measuring apparatus according to the present invention will be described hereunder with reference to the accompanying drawings. In this embodiment, the present invention is applied to an eye refractive power measuring apparatus for both subjective and objective use.

Figure 1:
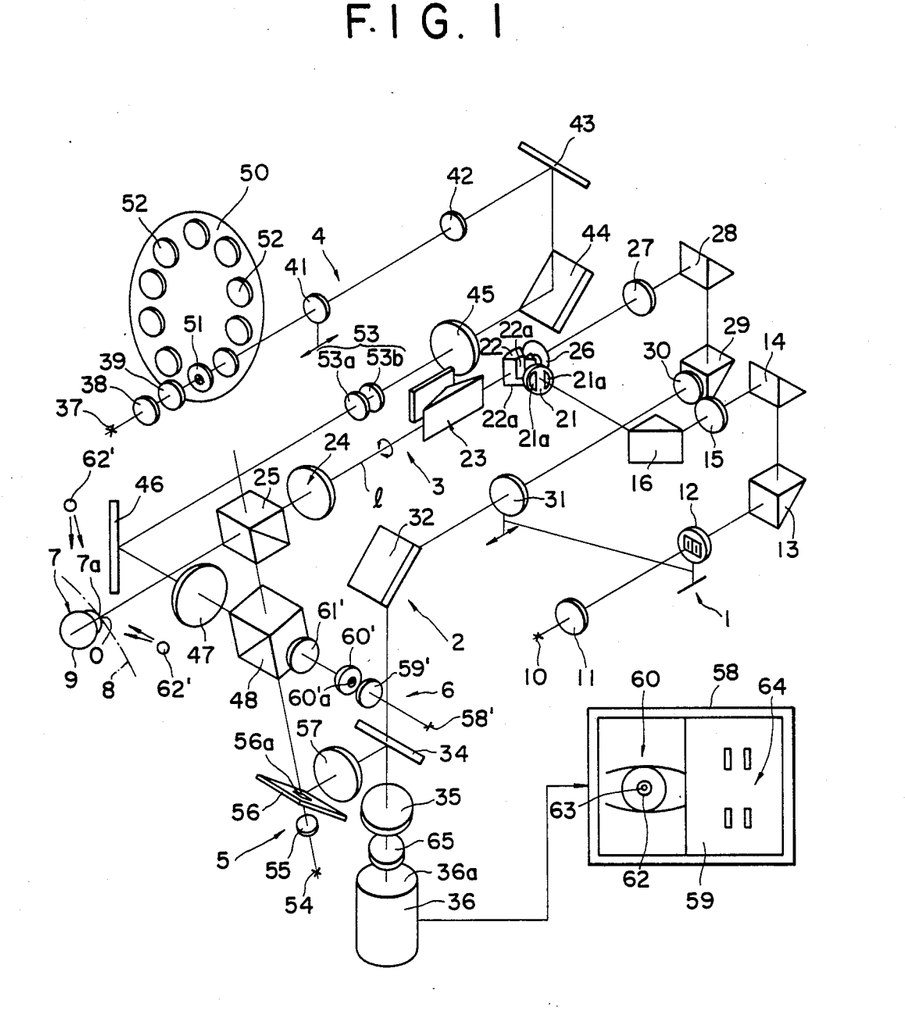
FIG. 1 is a schematic view showing an optical system of an eye refractive power measuring apparatus according to the present invention.
Figure 2:
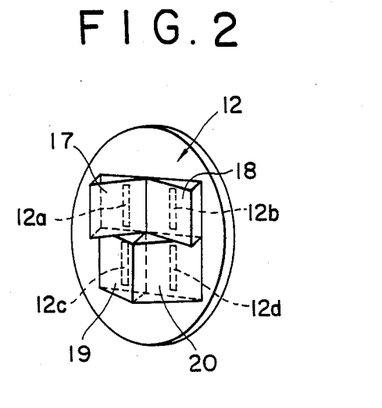
FIG. 2 is an enlarged perspective view showing the detailed constitution of a target plate shown in FIG. 1.

In FIG. 1, 1 denotes a target image projection system, 2 denotes an image forming optical system, 3 denotes a common use optical system which is commonly used for the target image projection system 1 and the image forming optical system 2, 4 denotes a chart projection system, 5, 6 denote sighting optical systems, 7 denotes an eye under test, and 8 denotes an anterior portion. The target image projection system 1 has such a function as that target light is projected to a retina 9 of the eye 7 under test through the common use optical system 3 and a target image is formed on the retina 9. The target image projection system 1 generally comprises a luminous element 10, a condenser lens 11, a target plate 12, reflection prisms 13, 14, a relay lens 15, and a reflection prism 16. The luminous element 10 emits infrared light having a central wavelength of 880 nm. The infrared light is converted to a parallel bundle of rays by the condenser lens 11 for luminating the target plate 12. The target plate 12, as shown in its enlarged state in FIG. 2, is formed with slits 12a through 12d. The target plate 12 is attached with four deflection prisms 17 through 20. Due to the foregoing, the target plate 12 is luminated by infrared light to form measuring target light, while the deflection prisms 17 through 20 deflect the target light in the perpendicular direction with respect to the longitudinal direction of the slit.

Figure 3:
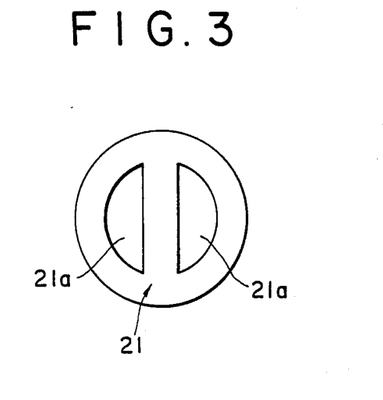
FIG. 3 is an enlarged plan view showing the configuration of a half moon diaphragm shown in FIG. 1.
Figure 4:
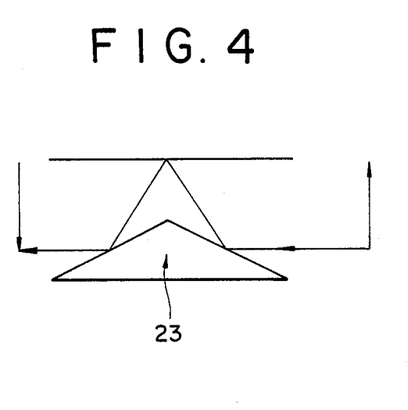
FIG. 4 is an enlarged plan view showing a rough configuration of an image rotator shown in FIG. 1.

On the other hand, the common use optical system 3 includes a half moon diaphragm plate 21, a slit prism 22, an image rotator 23, and a beam splitter 25. And, the target light formed by the target plate 12 is reflected by the reflection prisms 13, 14, 16 and guided to the half moon diaphragm plate 21. Then, the target light passes through half moon holes 21a, 21a as shown in the enlarged state in FIG. 3, is reflected by a reflection surface 22a of the slit prism 22, passes through a pupil of the eye 7 under test through image rotator 23, objective lens 24, and beam splitter 25 and is projected to the retina 9. The half moon diaphragm plate 21 is disposed in conjugate relation with the pupil position of the eye 7 under test which is in a proper position with respect to the objective lens 24 and adapted to enter the target light into the eye 7 under test in such a manner as to preventing harmful light to the measurement to be produced from the anterior portion 8 of the eye under test. The image rotator 23 which is shown in its plan shape in FIG. 4 is adapted to be rotated by angle of $\theta/2$ about the optical axis of the common use optical system 3 to rotate the measuring target image formed at the retina 9 by an angle of $\theta$ in the longitudinal direction of the eye 7 under test. The beam splitter 25 is adapted to reflect light within the wavelength of from 400 nm to 700 nm by 70%, reflect light within the wavelength of from 750 nm to 820 nm by 50% and transmit the target light (wavelength of 880 nm) by 100%. However, since the target light is invisible, contraction of the pupil due to the target image projection is prevented.

Figure 5:
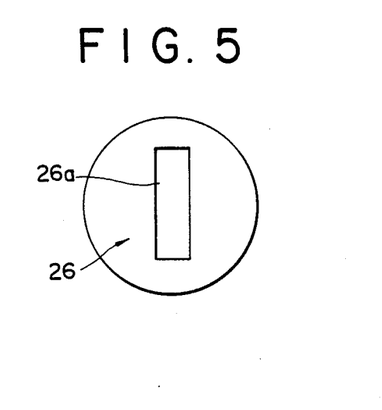
FIG. 5 is an enlarged plan view showing the configuration of an opening diaphragm shown in FIG. 1.

The reflection light of the measuring target image projected at the retina 9 is guided to the image forming optical system 2 through beam splitter 25, objective lens 24, slit hole 22a of the slit prism 22, opening 26a (see FIG. 5) formed at the central portion of the opening diaphragm plate 26, relay lens 27, and reflection prism 28. This opening diaphragm plate 26 is disposed in conjugate position with the pupil of the eye 7 under test and adapted to guide the reflection light which passes through the central portion of the pupil to the relay lens 27. The image forming optical system 2 generally comprises a reflection mirror 29, a stationary black dot plate 30, movable lens 31, a reflection mirror 32, a perforated mirror 34, and an imaging lens 35, and is adapted to guide the reflection light of the measuring target image formed at the retina 9 to the opto-electric surface 36a of an image pick-up apparatus 36 to form a measuring target image on the opto-electric surface 36a.

When the image rotator 23 is rotated about the optical axis 1 by angle of $\theta/2$, the measuring target image is rotated in the rotating direction by angle of $\theta$. However, since the reflection light of the measuring target image reflected by the retina 9 passes through the image rotator 23 again, the target image is rotated in the opposite direction to the rotating direction of the image rotator 23 by degree of $\theta$, and the opto-electric surface 36a of the pick-up image apparatus 36 is formed with the measuring target image facing toward a predetermined direction irrespective of the rotation of the image rotator 23. The black dot 30 is disposed at a position where harmful light reflected by the objective lens 24 is bundled. Due to the foregoing, the harmful reflection light which is harmful to the measurement is removed.

On the other hand, the chart projection system 4 generally comprises a tungsten lamp 37, a color correction filter 38, a condenser lens 39, a chart disk 50, a movable lens 41, a relay lens 42, reflection mirrors 43, 44, a relay lens 45, a reflection mirror 46, and an objective lens 47. The chart disk 50 is provided with a fixation chart plate 51 and various kinds of chart plates 52 for subjective measurement use. When the chart disk 50 is rotated, desired chart plates 51, 52 is inserted within the optical path. And, the chart disk 50 which is inserted within the optical path is illuminated by the tungsten lamp 37 through the condenser lens 39 and the color correction filter 38. The light emitted from the tungsten lamp 37 is selected its wavelength by the color correction filter 38. The correction filter 38 permits the light of wavelength from 400 nm to 700 nm to pass therethrough.

Figure 6:
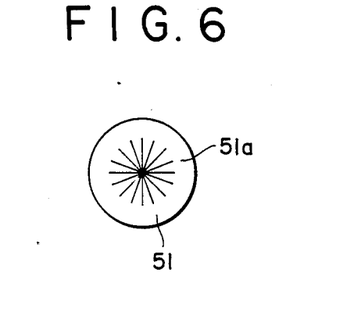
FIG. 6 is an enlarged plan view of a fixation chart plate shown in FIG. 1.
Figure 7:
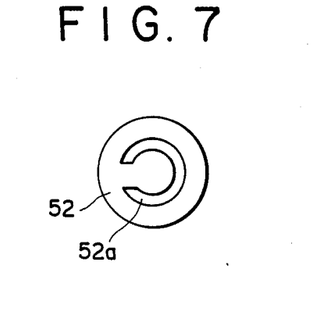
FIG. 7 is a plan view showing the configuration of a chart plate for subjective measurement use which is employed in an eye refractive power measuring apparatus according to the present invention.

The fixation chart plate 51 is provided with a fixation chart 51a as shown in FIG. 6. Light from the fixation chart 51a is guided to the movable lens 41 and the relay lens 42, turned its direction by the reflection mirrors 43, 44, 46; and guided to the beam splitter 48 passing through the objective lens 47. The beam splitter 48 has such a character as to reflect 75% of light of a wavelength in the visible range. The light from the fixation chart 51a is reflected toward the beam splitter 25 by the beam splitter 48, reflected by the beam splitter 25 and guided to the eye 7 under test. And, when refractive power of the eye 7 under test is automatically carried out in an objective fashion, the test is carried out while the patient gazes at the fixation chart 51a. When a subjective measurement is carried out, a chart plate 52 for subjective measurement use having a randolt ring 52a, etc. as shown for example in FIG. 7 is inserted within the optical path. The chart disk 50 is provided with a number of chart plates 52 for subjective measurement use having various patterns and configurations. When the chart disk 50 is rotated, a desired chart plate 52 is selectively inserted within the optical path, so that the patient may recognize it by sight. On the other hand, in FIG. 1, 53 denotes a cylindrical lens optical system. The cylindrical lens system 53 is disposed in generally conjugate position with glasses putting-on position of the eye 7 under test. The cylindrical lens system 53 will be described later. The movable lens 41 is movably disposed in its optical axis direction. At the time of objective measurement, the movable lens 41 is set in a position where the eye 7 under test is foggy sighted, so that the objective measurement is carried out in the state that the accommodation of the eye under test is removed. Instead of moving the movable lens 41, the chart disk 50 may be moved. In subjective measurement, the movable lens 41 or the chart disk 50 is moved according to response of the patient, and the refractive power of the eye under test is measured from the moving quantity.

The sighting optical system 5 includes an infrared light source 54 for emitting infrared light as an invisible light having a central wavelength of 800 nm, a projection lens 55 and a perforated mirror 56. The infrared light passes through the perforated mirror 56 and beam splitter 48, reflected by the beam splitter 25 and projected to the cornea 7a. And, when the optical axis of the common use optical system 3 is brought to be in alignment with the corneal vertex 0, the corneal vertex 0 is formed with a luminescent spot image of the infrared light emitted from the infrared light source 54. According to the foregoing, an alignment adjustment of the optical system with respect to the eye 7 under test is carried out. The infrared light forming the luminescent spot image is reflected on the corneal vertex 0, further reflected by the beam splitter 25, passes through the beam splitter 48, is turned its direction by the perforated mirror 56 and guided to the objective lens 57, reflected by the perforated mirror 34 and guided to the imaging lens 35, and forms an image as the luminescent spot image on the opto-electric surface 36a of the image pick-up apparatus 36. Since the infrared light is invisible, contraction of the pupil of the eye 7 under test is prevented.

The other sighting optical system 6 generally comprises an infrared light source 58 for emitting infrared light having a wavelength of 700 nm, a diffusion plate 59′, a scale plate 60′, and a projection lens 61′. The scale plate 60′ is formed with a circular-shaped through hole 60′a. The infrared light passing through the circular-shaped through hole 60′a becomes a scale image projection light. The scale image projection light is reflected by the beam splitter 48 and perforated mirror 56, guided to the objective lens 57, further reflected by the other perforated mirror 34, guided to the imaging lens 35, and formed as a circular-shaped scale image on the opto-electric surface 36a of the image pick-up apparatus 36 by the imaging lens 35. The beam splitter 48 reflects approximately 50% of the scale image.

On the other hand, the anterior portion 8 is luminated by luminous lamps 62′, 62′. The wavelength of the luminous light emitted from the luminous lamps 62′, 62′ is set to be 800 nm because of the reason as will be described later, and is different from that of the target light. Since the luminous light is also invisible, contraction of the pupil due to the luminous light is prevented. The anterior portion luminous light reflected on the anterior portion 8 is reflected by the beam splitter 25, passes through the beam splitter 48, is reflected by the perforated mirrors 56, 34, guided to the imaging lens 35, and formed as an anterior portion image on the opto-electric surface 36a of the image pick-up apparatus 36 by the imaging lens 35. In this embodiment, the reflection path of the luminescent spot image reflected on the corneal vertex 0 is the same as the reflection path of the luminous light reflected on the anterior portion 8. And, the scale image projection path and the reflection path of the luminous light reflected on the anterior portion 8 have a co-optical axis.

On the other hand, the image pick-up apparatus 36 is connected to a television monitor 58. 59 denotes its display surface. The display surface 59 is displayed an image formed on the opto-electric surface 36a based on video signal from the image pick-up apparatus 36. In FIG. 1, 60 denotes an anterior portion image, 62 denotes a circular-shaped scale image, 63 denotes a luminescent spot image, and 64 denotes a measuring target image. The tester can carry out the alignment adjustment of the optical system while confirming the positional relation among the anterior portion image 60, circular-shaped scale image 62, and luminescent image 63, respectively.

Figure 8:
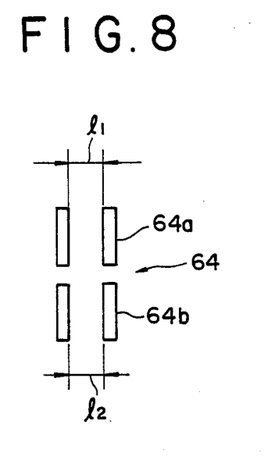
FIGS. 8 through 10 are plan views showing an image forming state of a measuring target image shown in FIG. 1.
Figure 9:
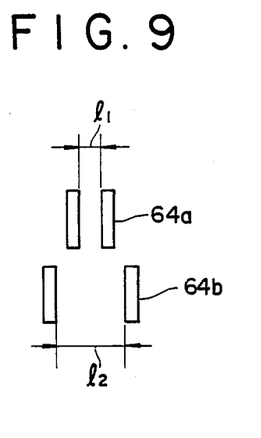
Figure 10:
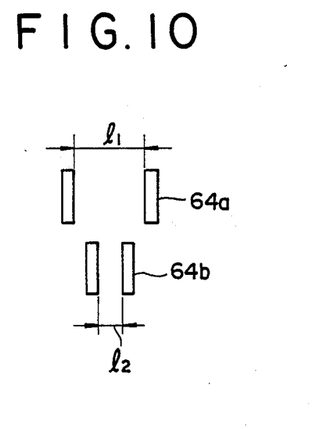

When the target image 64 is focused on the retina 9, target image 64 is in agreement in the space $l_1$ between a pair of target images 64a at its upper portion and the space $l_2$ between a pair of target images 64b at its lower portion as shown in FIG. 8. When the target image 64 is not focused on the retina 9, the space $l_1$ is different from the space $l_2$. For example, when the measuring target image is focused at a front portion of the retina 9, the space $l_1$ becomes smaller than the space $l_2$ as shown in FIG. 9. On the other hand, when the measuring target image is focused at a rear portion of the retina 9, the space $l_1$ becomes larger than the space $l_2$ as shown in FIG. 10. In objective measurement of the refractive power, the spaces $l_1$, $l_2$ are opto-electrically detected by a detection circuit 67 as will be described later, and the target plate 12 is automatically moved in such a manner as to bring the spaces $l_1$ and $l_2$ of the measuring target image 64 in alignment with respect to each other. Accordingly, the refractive power can be obtained from the moving quantity at the time when the target plate 12 is moved until the space $l_1$ and the space $l_2$ become identical with each other. At this time, the movable lens 31 is actuated in such a manner as to hold a conjugate relation integrally with the target plate 12.

Figure 11:
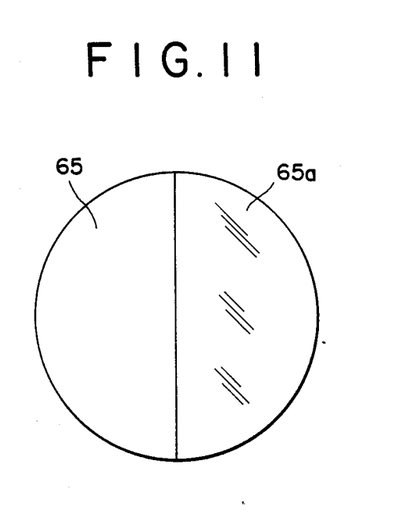
FIG. 11 is an enlarged plan view of a wavelength selection filter shown in FIG. 1.

The image forming optical system 2 is provided with a wavelength selection filter 65 between the imaging lens 35 and the image pick-up lens 36 and proximate to the opto-electric surface 36a of the image pick-up apparatus 36. The wavelength selection filter 65, as shown in FIG. 11, is formed at its left half portion with a transparent glass plate permitting light having a wavelength of 800 nm and light having a wavelength of 880 nm, and at its right half portion where a target image is to be formed with a deposition film 65a for wavelength selection use and adapted to permit light having a wavelength of 880 nm to pass therethrough and block light having a wavelength of 800 nm. According to the wavelength selection filter 65, since light forming the peripheral portion of the anterior portion image 60 is blocked by the deposition film 65a for wavelength selection use, the anterior portion image 60 is not projected one upon the other on the measurement target image 64. Accordingly, duplication of the anterior portion image 60 and the measuring target image 64 can be prevented. The perforated mirror 34 is adapted to form an image in order to displace the reflection light forming the anterior portion image at one side (the left side in FIG. 1) of the opto-electric surface 36a.

Next, a refractive power measurement circuit which is constituted by using a micro computer will be described.

Figure 12:
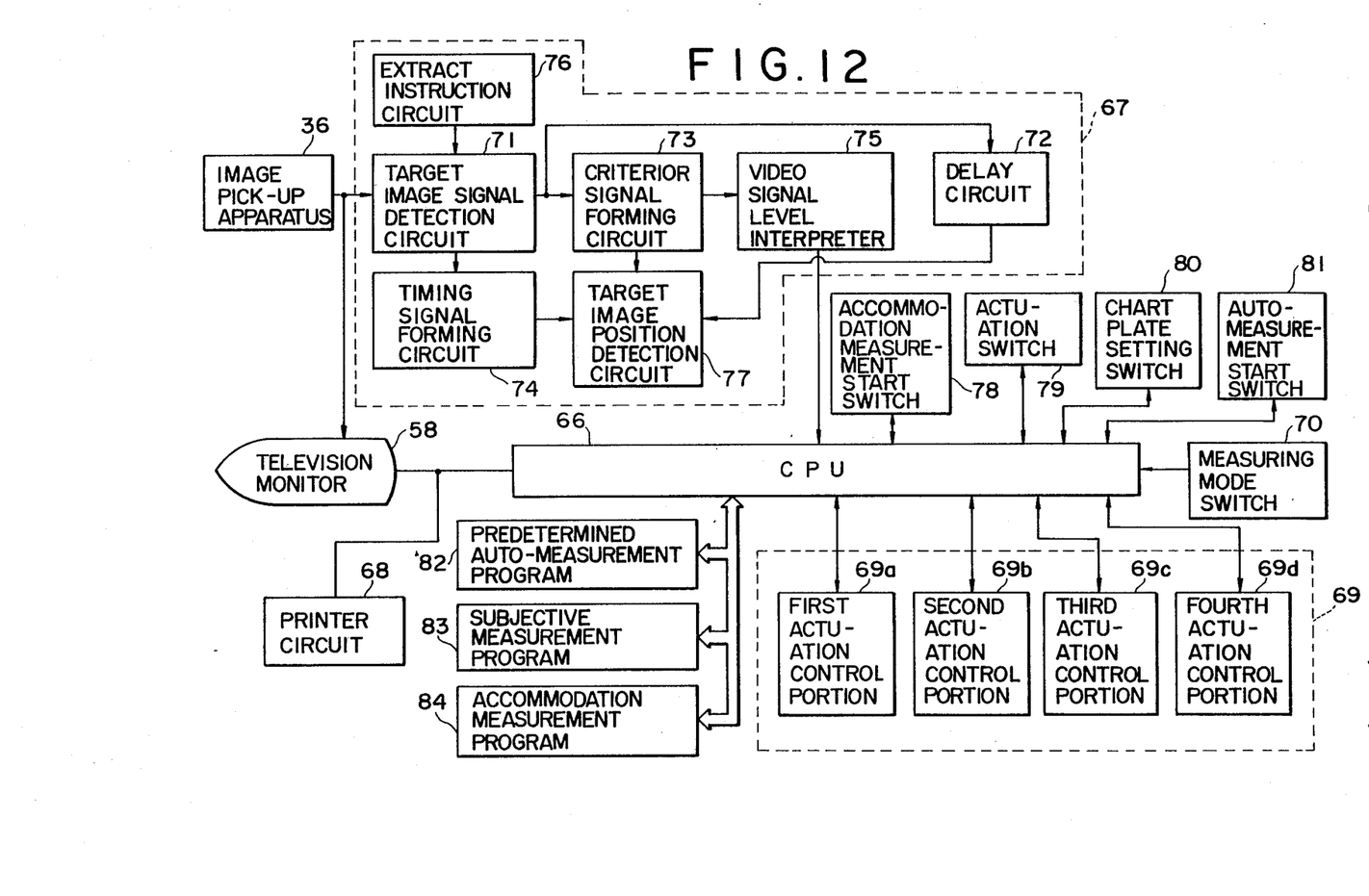
FIG. 12 is a block diagram of a measurement circuit which is employed in the eye refractive power measuring apparatus according to the present invention.

As shown in FIG. 12, CPU 66 forming the center of the micro computer is adapted to control a signal detection circuit 67 adapted to process video signal outputted from the image pick-up apparatus 36. Further, CPU 66 controls an actuation circuit 69 and is actuated by the switching of a measuring mode switch 70 for switching to either one control mode for the subjective measurement or the objective measurement. The measuring state, more particularly, the target image 64 is displayed in a visual image form from time to time by the television monitor 58 connected to the image pick-up apparatus 36 together with the anterior portion image 60 of the eye under test. The result of the measurement is printed out through a printer circuit 68.

In this embodiment, the signal detection circuit 67 comprises an extract instruction circuit 76 for generating extract instruction signal for extracting video signal for the measuring target image 64, a target image signal detection circuit 71 for detecting a target image by inputting the video signal emitted from the image pick-up apparatus 36, a delay circuit 72 for delaying the output from the target image signal detection circuit 71 for a predetermined time, a criterior signal forming circuit 73 for taking off criterior signal such as for example a rectangular-shaped wave corresponding to a criterior position of the target image based on the output from the target image signal detection circuit 71, a timing forming circuit 74 for generating a predetermined timing signal for forming an image based on the output from the target image detection circuit 71, a video signal level interpreter 75 for detecting light quantity level of the measuring target image 64 based on the rectangular wave obtained from the criterior signal forming circuit 73, and a target image position detection circuit 77 for establishing a target image position by receiving respective outputs from the delay circuit 72 and the timing signal forming circuit 74. Due to the foregoing, a signal distance or a space between the measuring target images 64 is detected at the target image position detection circuit 77.

On the other hand, CPU 66 controls an accommodation measurement start switch 78 to be manipulated when the accommodation measurement is started, an actuation switch 79 for moving the target plate 12 and the movable lens 31, a chart plate setting switch 80 to be manipulated when the fixation chart plate 51 and the chart plate 52 for subjective measurement use, and an auto-measurement start switch 81 for starting an auto-measurement, respectively. Further, CPU 66 controls the actuation control portion 69. The control portion 69 comprises a first actuation control portion 69a for moving the target plate 12 and the movable lens 31 along the optical axis, a second actuation control portion 69b for rotating the image rotator 23 about the optical axis, a third actuation control portion 69c for moving the movable lens 41 of the chart projection system 4 along the optical axis, and a fourth actuation control portion 69d for actuating the cylindrical lens optical system of the chart projection system 4. CPU 66 runs a predetermined auto-measurement program 82, subjective measurement program 83, or accommodation measurement program 84 already built therein.

Figures 13, 13B:
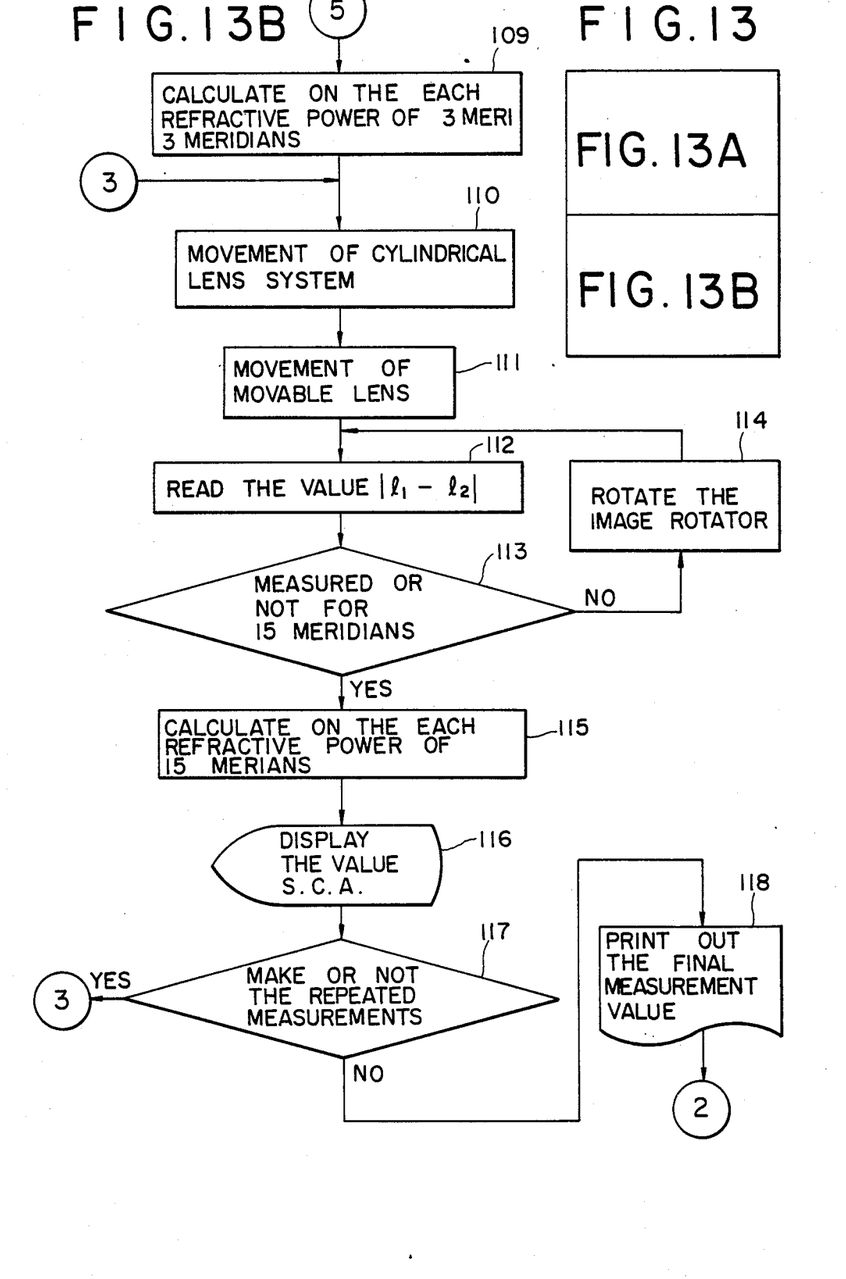
FIG. 13 is a flow chart for explaining the measuring order of the refractive power measuring apparatus of an ophthalmologic instrument according to the present invention.

Next, operation of an eye refractive power measurement apparatus according to the present invention will be described separately for cases of objective measurement and subjective measurement with reference to the flow chart shown in FIG. 13. In these cases, it is understood that the display surface 59 is simultaneously displayed with the anterior portion image 60 and the measurement target image 64.

The objective measurement will be described first. First of all, the run of calculative operation by CPU 66 is started upon charging of an power source, etc. When the auto-measurement start switch 81 is turned on, CPU 66 calls the auto-measurement program 82, a initial value setting is processed in STEP 100, and the first actuation control portion 69a is actuated by the initial value setting to bring the target plate 12 in a zero diopter position. And, the image rotator 23 is rotated about the optical axis 1 upon actuation of the second actuation control portion 69b to set an angle $\theta$ formed by a direction S intersecting at right angles with respect to the slit longitudinal direction of a target image to be formed on the retina 9 and a horizontal meridian h to be 45 degree (which is referred as the 45 degree meridian). And, the movable lens 41 is moved so that the patient can recognize by sight the fixation chart 51a at the zero diopter position upon actuation of the third actuation control portion 69c. Then, the cylindrical lens optical system 53 is set to zero diopter upon actuation of the fourth actuation control portion 69d.

Figure 13A:
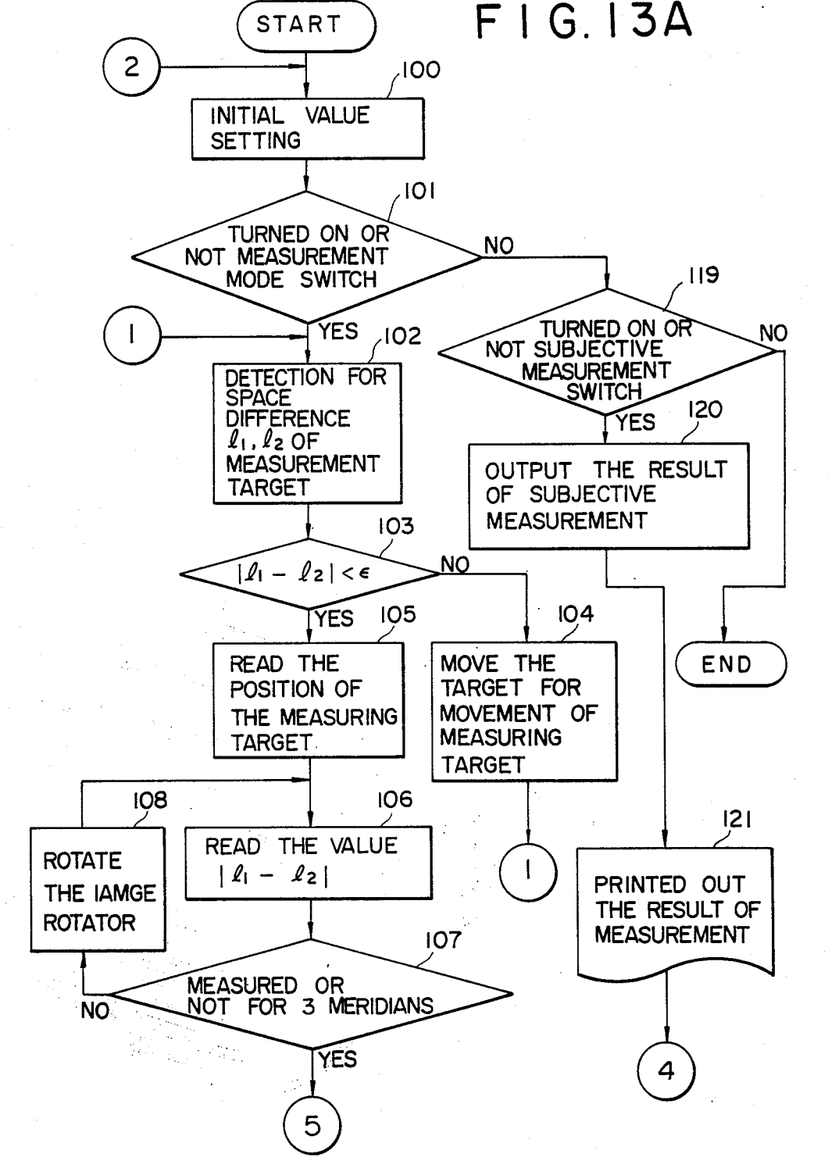

Next, with reference to FIG. 13A, when the measurement mode switch 70 is switched to the objective measurement mode, the judgment thereof is made in STEP 101. In the succeeding STEP 102, the spaces $l_1$, $l_2$ of the measuring target image are detected. In STEP 103, judgment is made on whether the space difference, $|l_1 - l_2|$ is smaller than a predetermined value $\epsilon$. And, if the space difference $|l_1 - l_2|$ is large than the predetermined value, the target plate 12 is actuated in such direction as to make the space difference $|l_1 - l_2|$ smaller than the predetermined value $\epsilon$ in STEP 104. At this time, the movable lens 31 is also moved together therewith to maintain the conjugate relation with the opto-electric surface 36a. And, STEPS 102, 103 and 104 are repeated until the space difference $|l_1 - l_2|$ becomes $|l_1-l_2|<\epsilon$. According to the movement of the target plate 12, the movable lens 41 is moved by the third actuation control portion 69c to maintain the foggy state for the patient. At this time, since both the anterior portion image 60 and measuring target image 64 are displayed on the display surface of the television monitor 58, the tester can observe the state under which the measurement is being carried out.

On the contrary, if the space difference $|l_1-l_2|$ becomes $|l_1-l_2|<\epsilon$, the position of the measuring target image is read in, in STEP 105. Subsequently, the space difference $|l_1-l_2|$ value is read in (STEP 106). CPU 66 effects a calculative operation (STEP 109) of the refractive power based on data obtained by the read-in operation (STEP 105) of the target image position and the read-in operation (STEP 106) of the space difference $|l_1-l_2|$ value. Owing to the foregoing, a refractive power of 45 degree meridian direction is obtained. In this embodiment, prior to the operation in STEP 109, the measuring target image is rotated by 60 degrees each time by rotating the image rotator 23 by 30 degree each time to obtain a refractive power for the respective 3 meridians (STEP 107).

Figure 14:
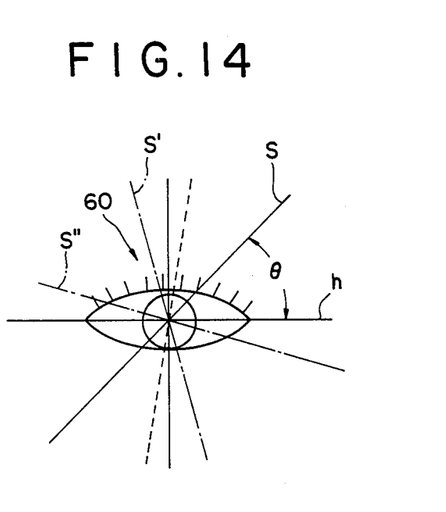
FIG. 14 is a schematic view for explaining the measuring order thereof.

In FIG. 14, S', S" denote directions intersecting at right angles the slit longitudinal direction, respectively when the measuring target image is rotated by 60 degree each time.

When the eye 9 under test is suffered from astigmatism, the measuring target image is separately detected according to the rotation of the image rotator 23. At this time, if the image rotator 23 rotated about the optical axis, it is known that a refractive power $D_\theta$ in the meridian angle direction is represented by the sum of a diopter value $D_\theta$ in a movement stop position of the target plate 12 and a diopter value $\Delta D_{74}$ corresponding to the diopter value $D_\theta$ and the slit separation quantity, and the following relative formula is obtained among a spherical power A, an astigmatism power B, and an astigmatism axis angle.

$$D_\theta = A + B \cos(\theta - \alpha)$$

Accordingly, if refractive powers $D_{\theta 1}$, $D_{\theta 2}$ and $D_{\theta 3}$ in 3 meridian directions are obtained the spherical power A, astigmatism power B and astigmatism axis angle power $\alpha$ can be obtained based on the following formulas.

$$D_{\theta 1} = A + B \cos 2(\theta_1 - \alpha)$$

$$D_{\theta 2} = A + B \cos 2(\theta_2 - \alpha)$$

$$D_{\theta 3} = A + B \cos 2(\theta_3 - \alpha)$$

Based on the calculation result of such obtained spherical power A, astigmatism power B and astigmatism angle power, the following main measurement is carried out.

In the main measurement, the meridian directions are further divided in smaller parts. For example, a measurement is effected with respect to 15 meridian direction. When the main measurement is carried out, the cylindrical lens optical system 53 is used. The cylindrical lens optical system 53 comprises a cylindrical lens 53a and another cylindrical lens 53b. When the pair of lens 53a, 53b are integrally rotated in the same direction at sam angles, the astigmatism axis is corrected, and the astigmatism power is corrected by rotating the lenses 53a, 53b in the opposite directions with respect to each other by equal angles. The cylindrical lens optical system 53 is controlled and established based on the calculation result of the astigmatism power B and the astigmatism axis angle $\alpha$, so that the fixation chart of the patient can be gazed evenly (STEP 110). Then, the movable lens 41 is moved to a position where the foggy state is maintained for the patient by the third actuation control portion 69c (STEP 111). Due to STEPS 110 and 111, the fixation chart is established corresponding to the refractive power of the eye under test, and the patient can gaze at the fixation chart evenly and in a correct foggy state. Then, the image rotator 23 is rotated at every 6 degrees and the measuring target image is rotated at every 12 degrees to measure refractive power $D_{\theta 1}$ through $D_{\theta 15}$ with respect to 15 meridian (STEPS 112 through 115). Based on the refractive power $D_{\theta 1}$ through $D_{\theta 15}$, the spherical power A, astigmatism power B and astigmatism axis angle $\alpha$ are calculated by means of the method for least squares, and the calculation result is displayed on the display surface (STEP 116). Since the astigmatism, when existed in the eye 7 under test, is corrected in this measurement, the fixation chart 15a is collimated. Therefore, a correct measurement result can be obtained in the state wherein no accommodation is acted on the eye 7 under test suffered from the astigmatism. Subsequently, a judgment is made on whether or not repeated measurements according to STEP 117 should be required. If required, the measurements of STEPS 110 THROUGH 116 are carried out again, and the final measurement value is printed out (STEP 118).

Next, operation of the subjective measurement will be described.

In the case of the subjective measurement, the switching to the subjective mode by means of the measuring mode switch 70 causes the subjective measurement program 83 to be called. And, the movable lens 41 is moved in the optical axis direction of the chart projection system 4 and established in its moving position based on the spherical power A of the eye 7 under test. And, the astigmatism power B is corrected by the cylindrical lens optical system 53. In the foregoing state, the chart disk 50 is rotated to insert a desired chart plate 52 for subjective measurement use within the optical path. That is, in the subjective measurement, the chart plate 52 for subjective measurement use is recognized by sight in the state wherein the refractive power obtained by the objective measurement is corrected.

In this way, the subjective measurement is effected while having the patient recognize by sight the chart plate 52 for subjective eyesight test use. The tester shows various kinds of chart plates 52 for subjective measurement use to the patient, actuates the movable lens 42 according to the response of the patient at that time to correct to spherical power A and actuates the cylindrical lens optical system 53 to correct the astigmatism axis angle $\alpha$ and the astigmatism power B. The foregoing actuation quantity is inputted into CPU 66, and the measurement result is printed out as a measurement value by STEPS 120 and 121. In this subjective measurement, a measurement target image of invisible light is always projected upon the chart image for subjective measurement use at the retina of the eye under test. At this time, the target plate 12 is always actuated to a position corresponding to the correction power by the chart projection system 4, and the focusing states of the chart image for subjective measurement use and the measuring target image are always maintained in alignment relation with respect to each other. In this case, since the tester can effect the subjective measurement while observing the target image in alignment in the focusing state with the chart image indicated on the display surface 59 of the television monitor 58 as a visible image, he knows with ease the state in which the patient is being tested while seeing the chart image by sight.

In the aforementioned embodiment, an eye refractive power measuring apparatus for both subjective and objective use has been described. However, it is understood that the present invention is applicable to an eye refractive power measuring apparatus for the exclusive use for the subjective type.

Figure 15:
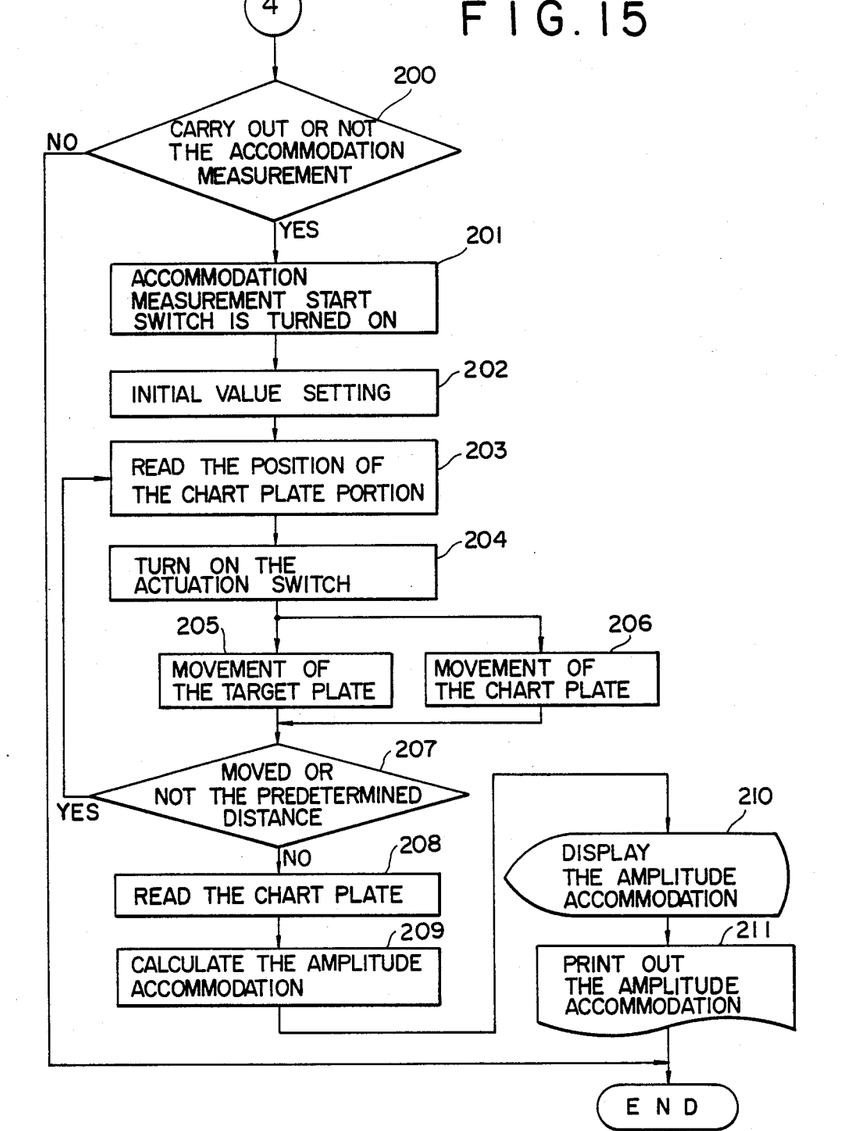
FIG. 15 is a flow chart for explaining the measuring order of the accommodation measurement.

Next, an accommodation measurement will be described with reference to a flow chart in FIG. 15.

First of all, in order to decide whether or not the program 84 of the accommodation measurement is run, it goes from either STEP 118 or STEP 121 to STEP 200. And, in STEP 201, when the accommodation measurement start switch 78 is turned on, CPU calls the accommodation measurement program 84, and the following accommodation measurement is carried out according to the program. In this accommodation measurement, the chart plate 51 of the chart projection system 4 functions as a chart plate for accommodation measurement use.

In running the program 84, firstly, the movable lens 41, target plate 12 and cylindrical lens optical system 53 are initially set in position corresponding to the refractive power for far use obtained by running the auto-measurement program. Due to the initial setting, the chart plate 51 and the target plate 12 are disposed in a generally far point position of the eye 6 under test, and a position scale (corresponding to the position of the movable lens 41) of the far point position is read in (STEPS 202, 203).

In this case, although the measuring target image of the invisible light and the chart image of the visible light are projected to the retina 9 of the eye under test in superposed relation, the patient can see only the chart image by sight. The patient can focus the point at the chart image in the far point position. At this time, the measuring target image on the display surface 59 of the television monitor 58 can be observed in a generally alignment relation in both the spaces $l_1$, $l_2$, as shown in FIG. 8.

Subsequently, the tester turns on the actuation switch 79 (STEP 204) to integrally move the target plate 12 and the chart plate 51 (or the movable lens 41) in the optical direction or near point direction in the synchronous state (STEPS 205, 206), so that the chart image and the measuring target image on the retina 9 will be changed in an identical focusing state, and the movement thereof is stopped at the time point when the measuring target image 64 on the indication surface 59 starts splitting as shown in FIG. 9 (STEP 207). BY regarding this time point as the near point position, the position scale is read in (STEP 208), The amplitude accommodation is calculated from the difference of the position scale between the near point position and the far point position (STEP 209), and the results are indicated on the television monitor 58 and recorded through the printer circuit 68 (STEP 210, 211).

As described in the foregoing, according to the first invention, the state of the target image which is in the identical focusing state with the chart image formed at the retina of the eye under test can be observed as an visible image even when the subjective type eye test is effected. Accordingly, the tester can understand with ease the state in which the patient gazes at the chart image. Thus, a correct eye test can be carried out. In addition, since the target image simultaneously projected with the chart image for subjective type test use uses invisible light, the target image can be observed without rendering any adverse affection to the subjective type eye test. In general, the chart image for the subjective type test use projected to the eye under test is extremely small and it is extremely difficult to observe the chart image itself. On the contrary, according to the first invention, since a target image of a free size and of a desired configuration can be projected separately from the chart image for the subjective type eyesight test use, an extremely easy observation is obtainable.

According to the second embodiment of the invention, the accommodation can be measured based on changes of the focusing state of the target image for measurement use according to changes of the focusing state of the chart image for test use. Accordingly, a objective measurement of the adjusting power is made possible. Thus, comparatively more correct measuring results are obtainable.

What is claimed is:

1. An eye refractive power measuring apparatus, comprising:
   chart projection means for projecting a chart image for test use to a retina of an eye under test by using visible light, said chart projection means including a chart plate disk having at least one first fixation chart for objective test use and a plurality of second fixation charts for subjective test use, said chart plate disk being manipulatable to selectively position one of said first and second fixation charts in an optical axis of said chart projection means;
   measuring target projection means for projecting a measuring target image to the retina of the eye under test by using invisible light;
   display device means for displaying said measuring target image as a visible image; and
   means for simultaneously changing a focusing state of said measuring target image and a focusing state of said chart image with respect to the eye under test.

2. An eye refractive power measuring apparatus, comprising:
   chart projection means for projecting a chart image for test use to a retina of an eye under test by using a visible light, said chart projection means including a chart plate disk having at least one first fixation chart for objective test use and a plurality of second fixation charts for subjective test use, said chart plate disk being manipulatable to selectively position one of said first and second fixation charts in an optical axis of said chart projection means;
   measuring target projection means for projecting a measuring target image to the retina of the eye under test by using invisible light;
   display device means for displaying said measuring target image as a visible image;
   means for simultaneously changing a focusing state of said measuring target image and a focusing state of said chart image with respect to the eye under test; and
   accommodation power measuring means for measuring amplitude of accommodation of the eye under test based on a change of focusing state of said measuring target image as observed on said display means and a change of focusing state of said chart image.

3. An eye refractive power measuring apparatus according to claim 2, wherein said target image projection means includes means for projecting a split measuring target image onto the retina of the eye under test.

4. An eye refractive power measuring apparatus according to claim 2, wherein said chart projection means includes a projection lens for projecting a bundle of rays from said chart plate to the retina of the eye under test to form said chart image, said focusing stat of said chart image of said chart plate being changeable by moving at least one of said chart plate and said projection lens along the optical axis of said projection means.

5. An eye refractive power measuring apparatus according to claim 4, wherein said accommodation measuring means includes a calculation means for objectively computing amplitude of accommodation of the eye under test in accordance with a movement distance obtained by moving at least one of said chart plate and said projection lens toward a near point direction from an initially set position, corresponding to refractive power for far distance accommodation, until said measuring target image observed on said display means is brought to be in a focusing state.

* * * * *